(12) United States Patent
Ham et al.

(10) Patent No.: US 8,338,445 B2
(45) Date of Patent: Dec. 25, 2012

(54) CRYSTAL FORM OF CABERGOLINE

(75) Inventors: Zoran Ham, Trbovlje (SI); Andrej Premrl, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 439 days.

(21) Appl. No.: 12/525,240

(22) PCT Filed: Jan. 30, 2008

(86) PCT No.: PCT/EP2008/051093
§ 371 (c)(1),
(2), (4) Date: Feb. 22, 2010

(87) PCT Pub. No.: WO2008/092881
PCT Pub. Date: Aug. 7, 2008

(65) Prior Publication Data
US 2010/0152223 A1  Jun. 17, 2010

(30) Foreign Application Priority Data

Jan. 31, 2007 (EP) .................................... 07101512

(51) Int. Cl.
*A61K 31/437* (2006.01)
*C07D 457/00* (2006.01)
(52) U.S. Cl. .......................................... 514/288; 546/69
(58) Field of Classification Search .................. 514/288; 546/69
See application file for complete search history.

(56) References Cited

U.S. PATENT DOCUMENTS 4,526,892 A    7/1985   Salvati et al.

FOREIGN PATENT DOCUMENTS

| GB | 2103603 A | 2/1983 |
|---|---|---|
| WO | WO-0170740 A1 | 9/2001 |
| WO | WO 01/72746 A | 10/2001 |
| WO | WO 01/72747 A | 10/2001 |
| WO | WO 03/078392 A | 9/2003 |
| WO | WO 03/078433 A | 9/2003 |
| WO | WO 2004/101510 A2 | 11/2004 |
| WO | WO-2004094368 A2 | 11/2004 |
| WO | WO-2005105796 A1 | 11/2005 |
| WO | WO-2006100492 A2 | 9/2006 |

OTHER PUBLICATIONS

Brambilla, Enzo et al.; "Synthesis and nidation inhibitory activity of a new class of ergoline derivatives"; Eur. J. Med. Chem.; 24(4); 1989; pp. 421-426.
Sabatino et al.; X-Ray Crystal Structure and Conformational Analysis of N-(3-Dimethylaminopropyl)-N-(Ethylaminocarbonyl)-6-(2-Propenyl) Ergoline-8β-Carboxamide (Cabergoline): Comparison with Bromocriptine and Lisuride and a Hypothesis for its high Dopaminergic Activity; Il Farmaco; 50(3); 1995; pp. 175-178.

*Primary Examiner* — Joseph K. McKane
*Assistant Examiner* — Samantha Shterengarts
(74) *Attorney, Agent, or Firm* — Arent Fox LLP

(57) ABSTRACT

The present invention relates to a cabergoline crystal form L, its preparation from halogenated aromatic solvents and aliphatic hydrocarbons and to pharmaceutical compositions containing the new form.

14 Claims, 8 Drawing Sheets

CRYSTAL FORM OF CABERGOLINE

CROSS-REFERENCE TO RELATED APPLICATION

This application is the National Stage of International Application No. PCT/EP2008/051093, filed Jan. 30, 2008, which claims benefit under 35 U.S.C. 119(a)-(d) or (f) or 365(b) of foreign application EP 07101512.7, filed Jan. 31, 2007, the contents of which are incorporated herein by reference in their entirety.

FIELD OF THE INVENTION

The present invention relates to a new crystal form of cabergoline, to processes for the preparation thereof and to pharmaceutical compositions containing it.

BACKGROUND OF THE INVENTION

Cabergoline is the generic name of the compound 1-((6-allylergolin-8β-yl)-carbonyl)-1-(3-dimethylaminopropyl)-3-ethylurea (Formula 1), Formula 1

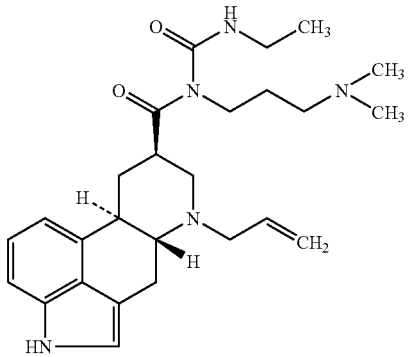

which belongs to the field of pharmaceutical agents for treatment of Parkinson's disease, restless legs syndrome, treatment of diseases like progressive supranuclear palsy and multisystematic atrophy. The compound was firstly described in the U.S. Pat. No. 4,526,892, Eur. J. Med. Chem., 24, 421 and GB-2,103,603-B reported the synthesis of cabergoline as well. II Farmaco, 50 (3), 175-178 (1995) firstly described crystalline cabergoline, later named cabergoline form I, which is unsolvated crystal form and was prepared as monocrystal from diethylether, Cabergoline was later described in several crystalline forms. The patent application WO 01/70740 describes form V as a toluene solvate and the process of its desolvatation into form I, WO 03/078392 describes form X as another toluene solvate and the process of conversion into form I. WO 01/72747 describes form II and its preparation. WO 01/72746 describes form VII and the process of preparing it. WO 04/101510 discloses amorphous cabergoline and several new crystalline forms of cabergoline such as form VIII (methyl tert-butyl ether solvate), form XI (xylene solvate), form XII (o-xylene solvate), form XIV (tetrahydropyrane solvate), form XV (cyclohexane solvate), form XVI (p-xylene solvate), form XVII (1,2,4-trimethylbenzene solvate), form XVIII (ethylbenzene solvate) and their preparation. WO 04/094368 discloses a new form of cabergoline (solvate form A (methyl tert-butyl ether solvate) and an amorphous form, free of crystalline cabergoline. WO 05/105796 describes an ethylbenzene solvate and WO 06/100492 several solvates with para disubstituted aromatic solvents as intermediates for preparation of form I. A process for preparing crystalline form I of cabergoline is described in WO 01/078433.

According to above mentioned literature cabergoline form I is in the form of plates, while repeating literature procedures for preparing form II and form VII gives agglomerates and thicker crystals. Crushing of hard thick crystals can lead to elevated temperatures which can decompose unstable material. Milling of softer material like the amorphous cabergoline often cause sticking of particles what lead to agglomerates and non-homogeneous material. On the other hand milling of the crystalline substance in the form of the needles using mechanical mills easily gives very fine material. Therefore, when low power is used for milling, the temperature of the substance during milling stays low and that prevents degradation of the product. There is no need for micronisation. Furthermore, when crystalline substance in the form of needles is used, this even means no milling in general, because the surface is not much enhanced by breaking needles as the longer side of the crystal possesses crucial part of the whole surface of needles. The surface of particles is responsible for physical contact in reaction environment what influences on the rate of dissolving and consequently on the dissolution profile and the kinetic parameters of a final dosage form.

It is generally known that the phenomena of agglomerates rarely appear in the case of crystal form where crystals are in the form of needles. Agglomerates include cavities which keep residual solvents and impurities from mother liquors. Removal of solvents and impurities from needles by washing and drying is easier and faster than from irregular particles and agglomerates what ensures better chemical quality.

Powdered and not agglomerated cabergoline is very suitable for preparation of the final dosage forms because it can be homogeneously incorporated into excipients what guarantees repeatable dissolution profile.

For pharmaceutical use there is a permanent need for preparation of active ingredients as much as possible free of impurities and solvents which are stable during technological operations of final dosage preparation and during storage up to its use for treatment in patients. Therefore the solvates with body unfriendly solvents are not suitable for pharmaceutical use, but only form I, form II and form VII are not characterized as solvates in literature. Thermodynamically stable crystal form is the most desirable form of active pharmaceutical ingredient from stability point of view. There is a constant need for preparation of thermodynamically stable cabergoline with low content of solvents. Said problem is solved within present invention disclosure.

SUMMARY OF THE INVENTION

The subject of the invention is a new form of cabergoline, crystalline cabergoline in the form of needles, designated cabergoline form L.

Another aspect of the invention is a process for the preparation of cabergoline form L comprising the following steps:
(a) dissolving cabergoline in a halogenated aromatic solvent and optionally in a co-solvent,
(b) cooling of the solution below 0° C. to obtain suspension,
(c) adding an anti-solvent,
(d) re-warming the solution above 0° C.,
(e) isolating the precipitated product.

Another aspect of the invention is a process for the preparation of cabergoline form L comprising the following steps:

(a) preparation of semi-solid cabergoline via extraction of crude cabergoline, first dissolved in the water/acetonitrile mixture from said mixture into dichloromethane organic phase and evaporation of organic solvents to obtain semi-solid cabergoline (b) dissolving semi-solid cabergoline in a halogenated aromatic solvent and optionally a co-solvent (c) cooling of the solution below 0° C. to obtain suspension (d) adding an anti-solvent (e) rewarming the solution above 0° C.

(f) isolating the precipitated product

Another aspect of the invention is cabergoline form L used for the preparation of pharmaceutical composition.

Another aspect of the invention is a method for preparing a pharmaceutical composition comprising combining an amount of cabergoline form L and at least one pharmaceutical acceptable carrier.

Another aspect of the invention is a pharmaceutical composition comprising cabergoline form L used for a treatment of Parkinson's disease, restless legs syndrome and treatment of progressive supranuclear palsy and multisystematic atrophy and for treating D2 dopamine receptor associated disorders.

DETAILED DESCRIPTION OF THE INVENTION

The subject of the invention is a new, well defined and for a long term stable crystal form of cabergoline designated cabergoline form L. It is an unsolvated form and exhibits great thermodynamical stability. It is the first known cabergoline form that appears in the shape of needles.

Cabergoline crystal form L in accordance with the invention is characterized by d-values 4.1; 5.9; 6.1; 7.4; 8.4; 12.3 in X-Ray diffraction pattern.

Figure 1:
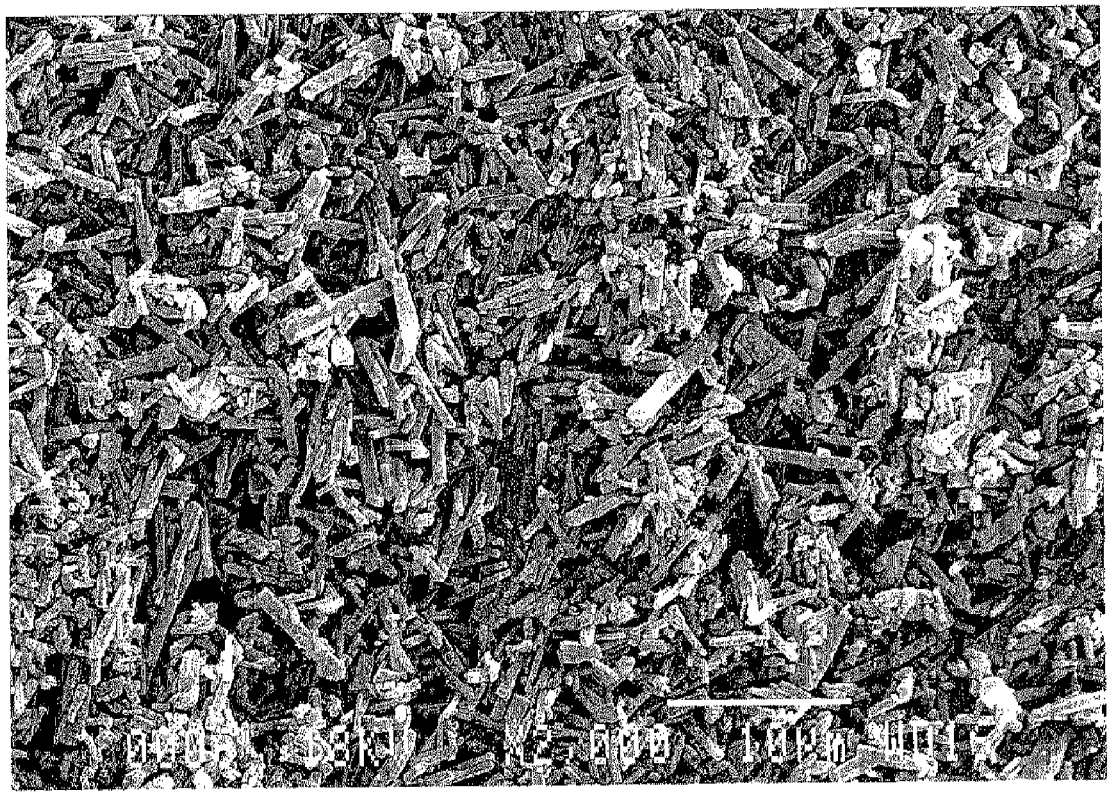
FIG. 1: SEM Picture of cabergoline form L prepared by Example 2.
Figure 2:
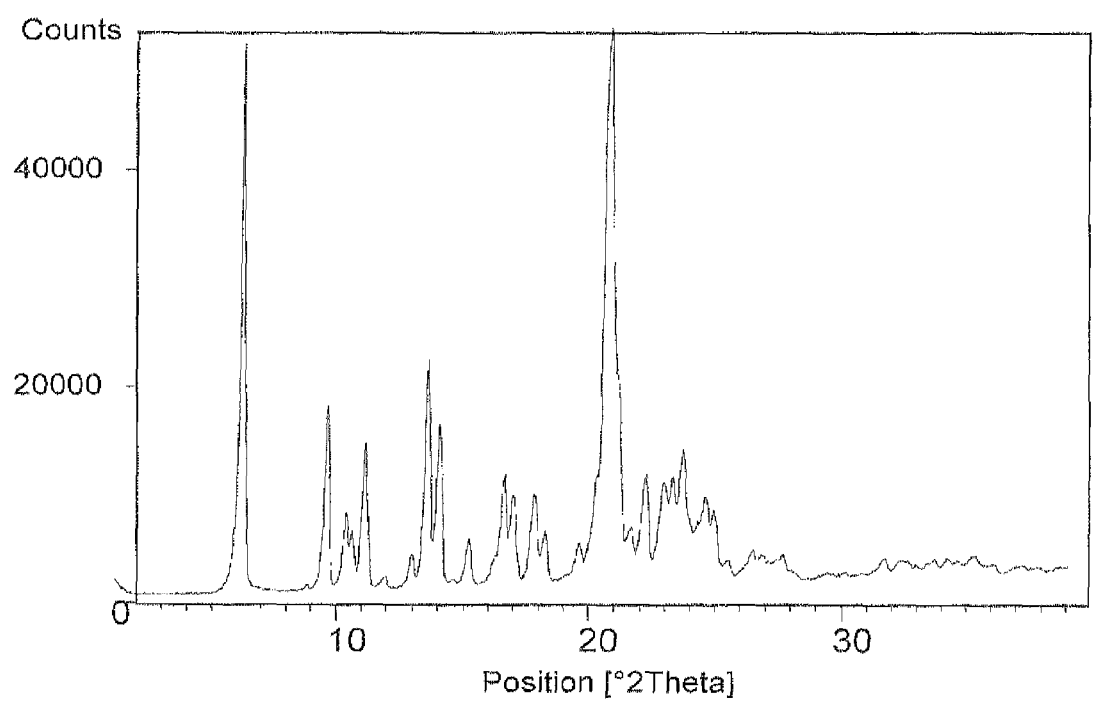
FIG. 2: X-ray powder diffraction pattern of cabergoline form L prepared by Example 2.
Figure 3:
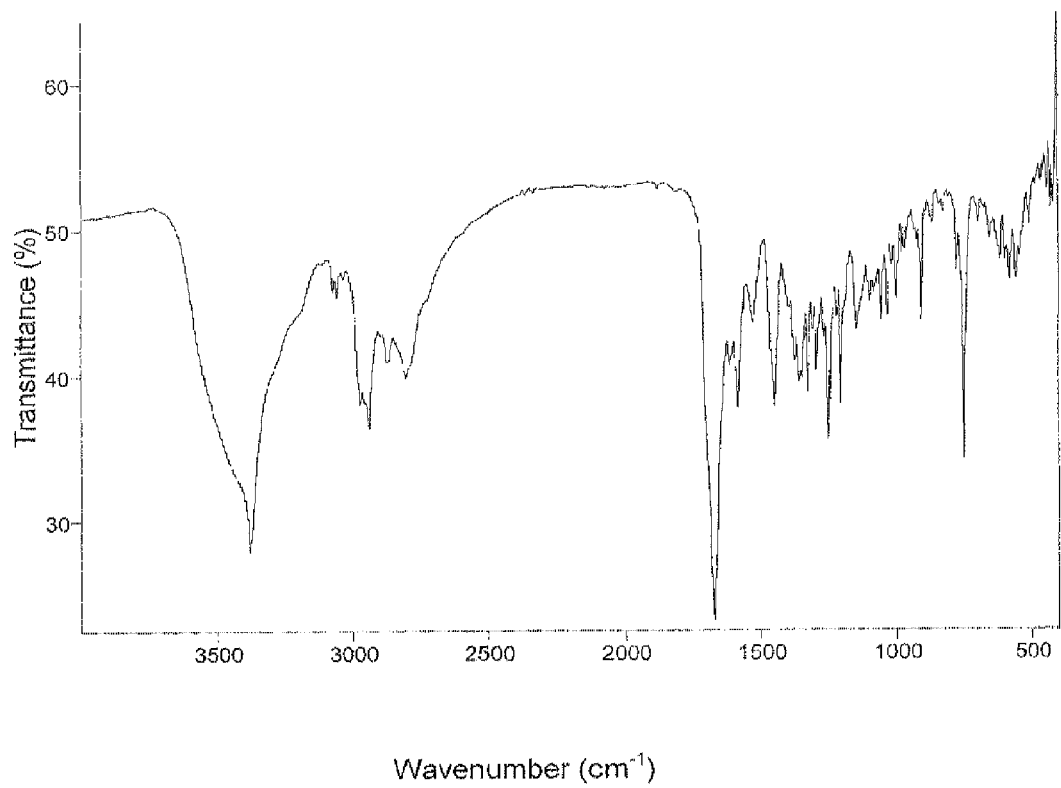
FIG. 3: Infrared spectrum of cabergoline form L prepared by Example 2.
Figure 4:
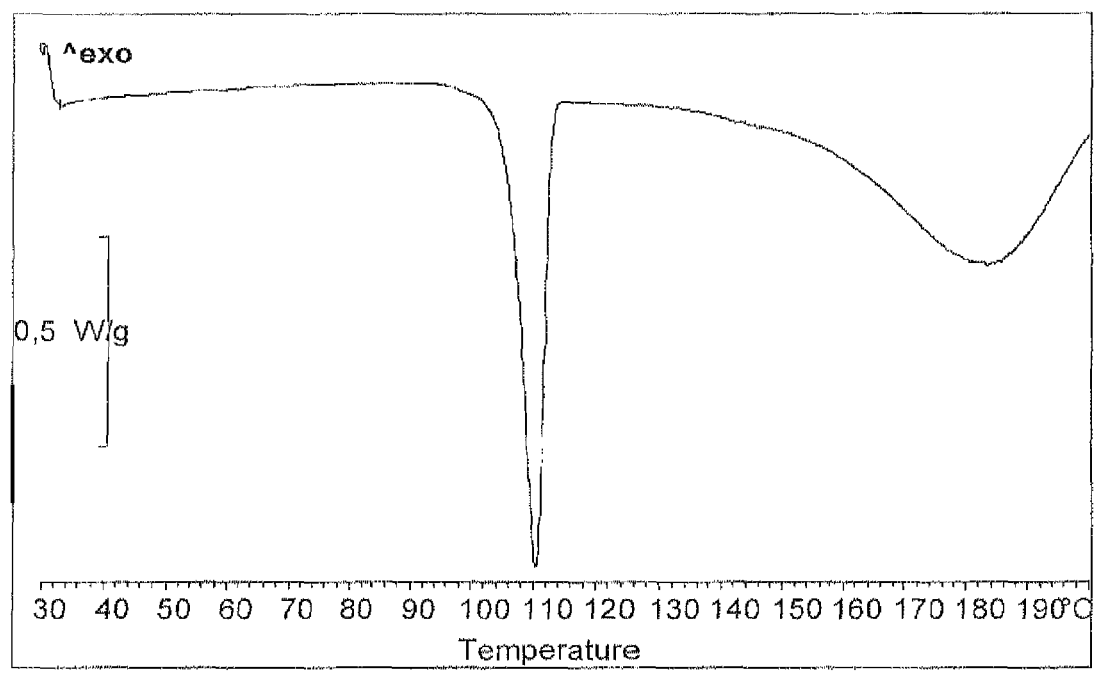
FIG. 4: Differential scanning calorimetry pattern of cabergoline form L prepared by Example 2.
Figure 5:
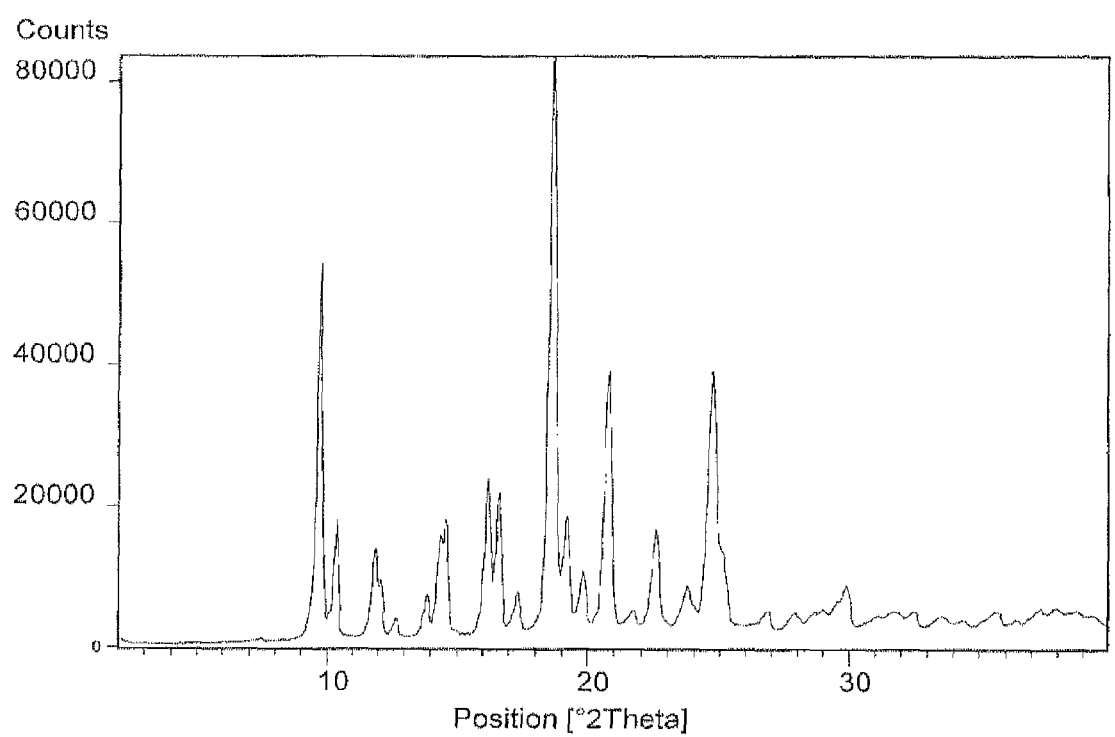
FIG. 5: X-ray powder diffraction pattern of cabergoline form I prepared by Example B.
Figure 6:
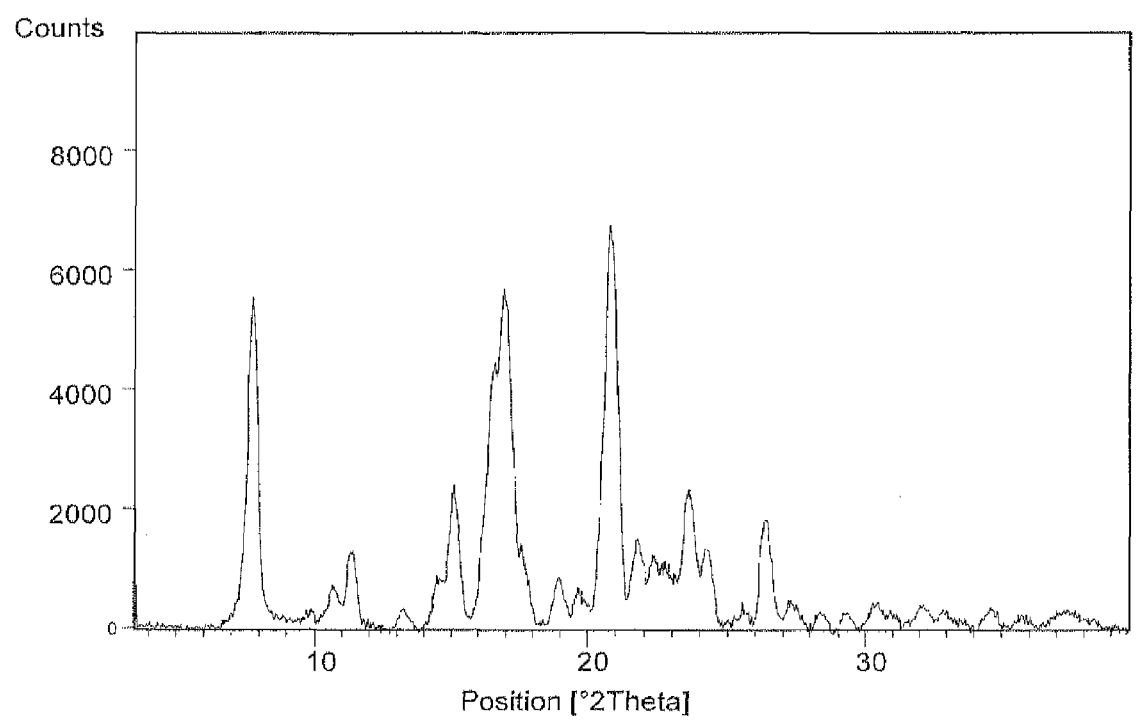
FIG. 6: X-ray powder diffraction pattern of cabergoline 2-chlorotoluene solvate prepared by Example A.
Figure 7:
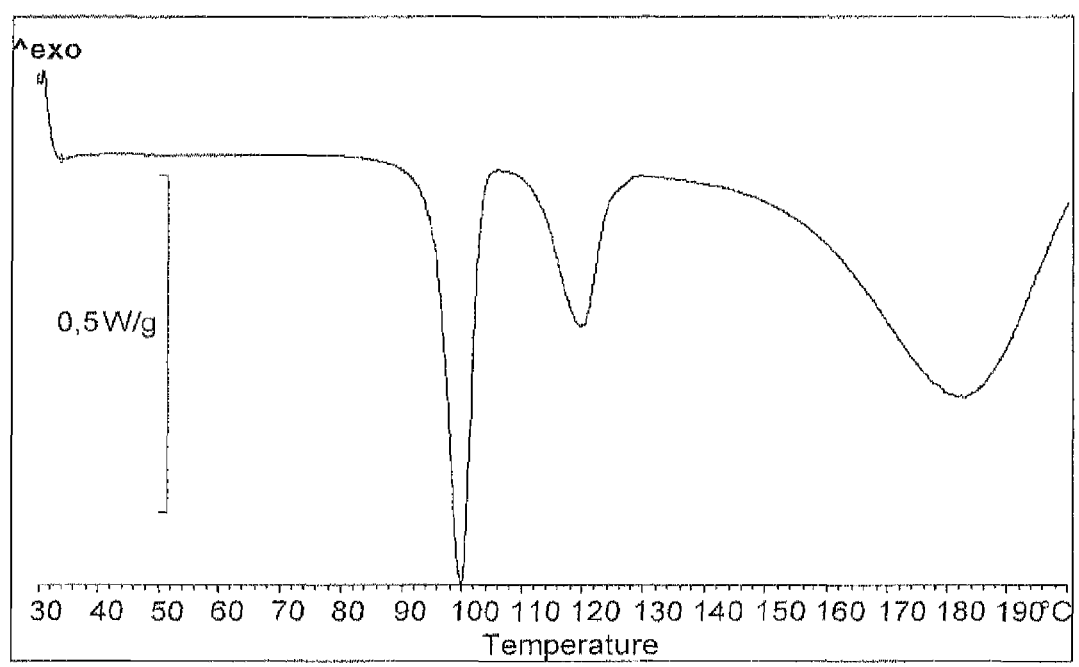
FIG. 7: Differential scanning calorimetry pattern of precipitate of Example B.
Figure 8:
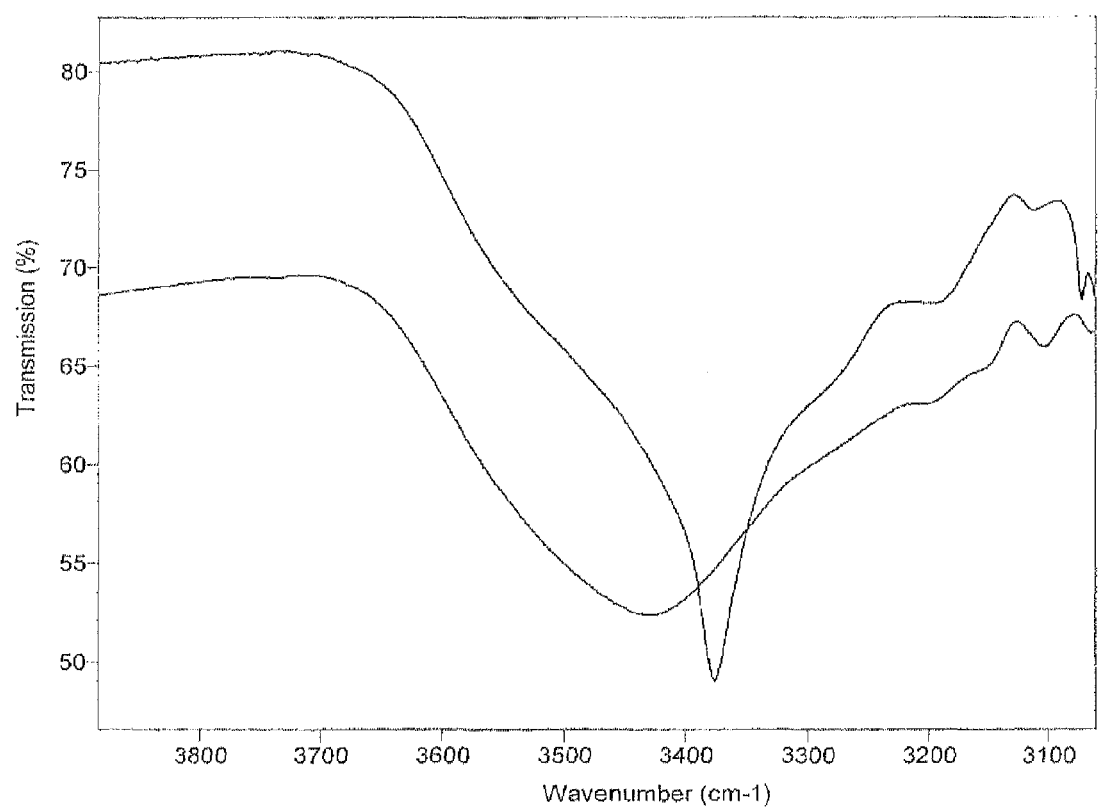
FIG. 8: Characteristic peak of cabergoline form L at 3377 cm$^{-1}$ (prepared by Example 2) in IR spectrum compared with form I (prepared by Example B).

Cabergoline crystal form L in accordance with the invention can also be characterized by an X ray diffration pattern shown in FIG. 2.

Cabergoline crystal form L in accordance with the invention can also be characterized with a characteristic peak in IR spectrum at about 3377 cm$^{-1}$.

Cabergoline crystal form L in accordance with the invention can also be characterized with endothermic peak with onset between 105 and 107° C.

The present invention also provides a simple and efficient process for the preparation of cabergoline form L with high yields and low amount of impurities.

Cabergoline form L can be prepared by precipitation from a mixture of aromatic solvents preferably halogenated aromatic solvents, and aliphatic hydrocarbons as anti-solvents. Starting material can be crude cabergoline or cabergoline in any form.

Semi-solid cabergoline can be prepared by the known procedure disclosed in the literature (Eur. J. Med. Chem. 24 (1989), 421) and can be additionally purified by chromatography followed by evaporation of the eluting solvents to obtain, amorphous material, semi-solid or oil or mixture thereof.

Halogenated aromatic solvent can be selected from a group of fluoro, difluoro or chloro substituted benzene, preferably chloro substituted benzene and toluene, preferably chlorobenzene and 2-chlorotoluene, most preferably 2-chlorotoluene.

Optionally, said halogenated aromatic solvents can be combined with low amounts of a water miscible aprotic solvent such as acetonitrile or acetone as co-solvents.

As an anti-solvents aliphatic hydrocarbons such as pentane, heptane or hexane (C5-C7 alkanes) can be used, which cause lowering the solubility of cabergoline in abovementioned aromatic solvents with optionally addition of the co-solvent, at ambient temperatures.

A process for the preparation of pure cabergoline form L according to the present invention comprises the steps of:

preparation of semi-solid cabergoline via extraction of crude cabergoline, first dissolved in the water/acetonitrile mixture from said mixture into dichloromethane organic phase and evaporation of organic solvents to obtain semi-solid cabergoline, dissolving of semi-solid cabergoline in aromatic solvent, preferably chloroaromatic solvent e.g. 2-chlorotoluene or in the mixture of aromatic and chloroaromatic solvents and lowering the temperature below −25° C. precipitating solid material to obtain suspension, addition of alkane such as pentane, heptane or hexane for lowering the solubility of cabergoline in solvents used in step (b) at low temperature followed by gradual warming the mixture to room temperature, (a) isolating of cabergoline form L at ambient temperature.

Starting crude cabergoline is prepared by any known process, preferably as described in Example 1. Cabergoline is isolated by extraction and further purified by chromatography, e.g. in silica gel column with mobile phase of ketones, preferably acetone or lower alcohols preferably ethanol. The obtained solution is evaporated to the oily, foamy or semi-solid material of amorphous cabergoline by evaporation. Alternatively crude cabergoline can be purified by preparative HPLC on the reverse stationary phase to yield acetonitrile/water or alcohol/water solution of cabergoline preferably acetonitrile/water which was concentrated and extracted with organic solvent, preferably dichloromethane. Starting material for the process of invention is isolated by evaporation as semi-solid amorphous material.

Starting semi-solid cabergoline must be dissolved in the aromatic solvent as quick as possible after the preparation due to instability of amorphous material.

Aromatic solvent in which the starting semi-solid cabergoline is dissolved is preferably halogenated aromatic solvent. Halogenated aromatic solvent is selected from a group of fluoro, difluoro or chloro substituted benzene, preferably chloro substituted benzene and toluene, preferably chlorobenzene and 2-chlorotoluene, most preferably 2-chlorotoluene. Said halogenated aromatic solvent can be optionally mixed with co-solvent. The co-solvent is selected from water immiscible solvents such as esters, ethers and aromatic hydrocarbons or water miscible aprotic solvents such as ketones and nitriles, preferably acetone and acetonitrile. An amount of the halogenated aromatic solvent used is from 2 to 5 ml of solvent per gram of cabergoline. An amount of the additional solvents is between 0 and 10 w/w % per total mass of solvents, preferably between 0 and 5%. Afterwards the obtained solution is cooled down below −10° C., preferably to −15 to −30° C., more preferably to −25° C. and let stand or stirred for at least 1 hour. During this period a precipitation occurs. The mixture can be diluted by an anti-solvent which lowers the solubility of cabergoline in a previously used aromatic preferably chloro substituted aromatic solvents. This anti-solvent is selected from aliphatic hydrocarbons preferably used are selected from the group of from solvents such as n-heptane, n-hexane, n-pentane, cyclopentane, cyclohexane or methylcyclohexane, most preferably from n-heptane and used amount of anti-solvent is 20 ml per gram of cabergoline. After the anti-solvent is added the mixture is further stirred for 2 to 12 hours, preferably 2 hours at the temperature −10 to −30° C., preferably at −15 to −25° C., more preferably at −20° C. The obtained suspension is afterwards heated to 5 to 30° C., preferably to 10° C. and let stirred for 2-3 days, preferably 1-24 hours, most preferably 6 hours at said temperature. Formation of cabergoline form L can be controlled by IR spectroscopy. When the IR spectrum shows that all cabergoline is in form L the product can be isolated. The obtained crystals are isolated by removing of the solvents preferably by filtration, decantation or centrifugation, most preferably by filtration at ambient temperature are finally washed with said aliphatic hydrocarbons. The obtained solid cabergoline substance is identified as cabergoline form L.

Another process for the preparation of cabergoline form L according to the present invention comprises the steps of:
  dissolving solid cabergoline of any form in aromatic solvent, or in a mixture of aromatic solvent and small amount of co-solvent such as acetonitrile or acetone and lowering the temperature below −25° C. and precipitating out solid material to obtain suspension
  addition of alkane such as pentane, heptane or hexane for lowering the solubility of cabergoline in solvents used in step (a) at low temperature followed by gradual warming the mixture to room temperature
  isolating of cabergoline form L at ambient temperature.

Any form of cabergoline in step (a) means solid cabergoline selected from a group of solvates with aromatic solvents, above mentioned known crystal forms I, II and VII or also from amorphous form of cabergoline.

Cabergoline of any form is dissolved in the aromatic solvent preferably halogenated aromatic solvent more preferably chloroaromatic solvent, most preferably 2-chlorotoluene in a volume of 2 to 5 ml of solvent per gram of cabergoline. Solid cabergoline is selected from solvates with ethers and aromatic solvents, non solvated forms I, II and VII and solid amorphous form. Optionally, the same co-solvents can be used as described within previous procedure. An amount of co-solvent is between 0 and 10 w/w % per total mass of solvents, preferably between 0 and 5%, the temperature of dissolving process is high enough to dissolve the solid cabergoline and is between 0 and 80° C., preferably between 10 and 30° C. Afterwards the obtained solution is coded down below −10° C., preferably to −15 to −30° C., more preferably to −25° C. and let stand or stirred for at least 1 hour at said temperature. During this period a precipitation occurs. The mixture can be diluted by an anti-solvent which lowers the solubility of cabergoline in a previously mentioned chloroaromatic solvent. This anti-solvent is selected from aliphatic hydrocarbons preferably from solvents such as n-heptane, n-hexane, n-pentane, cyclopentane, cyclohexane or methylcyclohexane, preferably from n-heptane in amount of 20 ml per gram of cabergoline. After the anti-solvent is added the mixture is further stirred for 2 to 12 hours, preferably 2 hours at the temperature −10 to −30° C., preferably to −15 to −25° C., more preferably to −20° C. The obtained suspension is further heated to 5 to 30° C., preferably 10° C. and let stirred for 2-3 days, preferably 1-24 hours, most preferably 6 hours. The obtained crystals are isolated by removing of the solvents preferably by filtration, decantation or centrifugation, most preferably by filtration at ambient temperature with washing with hydrocarbons. The obtained solid cabergoline substance is identified as cabergoline form L.

Following the processes according to the invention physically pure cabergoline form L is isolated. Shortening of the stirring period at temperature above 0° C. or isolation of solids at temperatures below 5° C. or considerable changing solvent/anti-solvent ratio may cause mixtures of various forms or other forms. Differential Example A describes isolation of a precipitate at −25° C. which is proved to be cabergoline 2-chlorotoluene solvate. Differential Example B describes capturing of a precipitate between 5-10° C. optionally after quick recooling to between −15 and −30° C. in which various mixtures of form I and form L were isolated in which the contain of form I in form L is from 0 to 100%.

Physically pure cabergoline form L is isolated in a form of fine needles what is shown in the SEM picture. Average shorter axis of the needles is below 10 μm. Milling of cabergoline form L isolated by the process of the invention by a hammer mill gives particle size distribution d 0.9 below 10 μm.

Cabergoline from L isolated by the process of the invention can be washed by cold aliphatic hydrocarbons or digesting previously isolated material in a suspension of aliphatic hydrocarbons preferably heptane to remove impurities and finally dried in vacuo at temperature from 20 to 80° C., preferably from 30 to 50° C., preferably 30 to 40° C. to remove residual solvents. Table 1 shows containment of residual solvents of heptane and 2-chlorotoluene after comparable drying of form L and form I at 35° C. at 5 mBar for 48 h. Form L and form I are isolated from the same solvent mixture, but form I is captured as an early precipitate as described in Example B and contains below 5% of form L. Solvents are easier removed if cabergoline is in the form of needles.

TABLE 1

|  | Heptane | 2-Chlorotoluene |
|---|---|---|
| Cabergoline form L (needles) | 186 ppm | 236 ppm |
| Cabergoline form I (irregular) | 764 ppm | 333 ppm |

In Table 2 the characterization of Cabergoline form L by the following characteristic peaks in XRD diffractogram (FIG. 2) with values is shown.

TABLE 2

| °2θ | d (Å) | Rel. Int. (%) |
|---|---|---|
| 7.17 | 12.33 | 100 |
| 10.53 | 8.40 | 33 |
| 11.26 | 7.86 | 14 |
| 11.50 | 7.70 | 14 |
| 12.03 | 7.36 | 26 |
| 12.81 | 6.91 | 2 |
| 13.87 | 6.39 | 6 |

TABLE 2-continued

| °2θ | d (Å) | Rel. Int. (%) |
|---|---|---|
| 14.52 | 6.10 | 41 |
| 14.98 | 5.92 | 29 |
| 16.13 | 5.50 | 8 |
| 17.53 | 5.06 | 20 |
| 17.89 | 4.96 | 16 |
| 18.76 | 4.73 | 15 |
| 19.18 | 4.63 | 9 |
| 20.54 | 4.32 | 6 |
| 21.20 | 4.19 | 27 |
| 21.64 | 4.11 | 88 |
| 21.80 | 4.08 | 98 |
| 22.07 | 4.03 | 55 |
| 22.55 | 3.94 | 9 |
| 23.13 | 3.85 | 18 |
| 23.85 | 3.73 | 17 |
| 24.62 | 3.62 | 23 |
| 25.89 | 3.44 | 11 |

These values are more exactly confirmed by analyzing a monocrystal isolated from longer standing mother liquors and are shown in Table 3.

TABLE 3

| °2θ | d (Å) |
|---|---|
| 7.20 | 12.27 |
| 10.58 | 8.36 |
| 11.31 | 7.83 |
| 11.56 | 7.65 |
| 12.06 | 7.34 |
| 12.88 | 6.88 |
| 13.93 | 6.36 |
| 14.57 | 6.08 |
| 15.04 | 5.89 |
| 16.20 | 5.47 |
| 17.58 | 5.04 |
| 17.95 | 4.94 |
| 18.81 | 4.72 |
| 19.23 | 4.62 |
| 20.60 | 4.31 |
| 21.24 | 4.18 |
| 21.66 | 4.10 |
| 21.88 | 4.06 |
| 22.16 | 4.01 |
| 22.61 | 3.93 |
| 23.23 | 3.83 |
| 23.93 | 3.72 |
| 24.68 | 3.61 |
| 25.98 | 3.43 |

The melting point of cabergoline form L is determined with DSC method with endothermic peak with onset between 105 and 111° C., preferably between 105 and 107° C. In a specific example Example 2 using apparatus described below the product showed onset at 106.4° C. and enthalpy of 57.1 J/g.

The characteristic peak of cabergoline form L in IR spectrum appeared at 3377 cm$^{-1}$.

Cabergoline form L prepared according to this invention can be used for the preparation of pharmaceutical composition. A pharmaceutical composition can be prepared from cabergoline form L and at least one pharmaceutical acceptable carrier. Pharmaceutical composition comprising cabergoline form L prepared according to this invention can be used for a treatment of Parkinson's disease, restless legs syndrome and treatment of progressive supranuclear palsy and multisystematic atrophy and for treating D2 dopamine receptor associated disorders.

The embodiment of the invention is characterized but not limited by the following experimental examples.

Example 1

Preparation of Crude Cabergoline 17 g of (9R)-7-allyl-4,6,6a,7,8,9,10,10a-octahydroindolo [4,3-fg]quinoline-9-carboxylic acid were suspended in 300 ml of dimethylformamide. 20.6 g of N-(3-dimethylaminopropyl)-N'-ethylcarbodiimide hydrochloride were added and 18.2 ml of ethyldiisopropylamine were slowly added drop wise in the reactor vessel. The mixture was stirred for 30 hours at room temperature. The solvent was evaporated when the reaction was finished. Further 60 ml of dichloromethane was added and the obtained solution was washed with 2 portions of 40 ml of 2% water solution of ammonia, 2 portions of 40 ml of water and 40 ml of 10% water solution of NaCl. First two alkaline solutions are extracted again with another 30 ml of dichloromethane and evaporated. The obtained crude cabergoline was purified on the RP-18 column with mobile phase of acetonitrile/water. The obtained solution was extracted with dichloromethane at pH=7. Organic phase was evaporated to the oily, foamy or semi-solid material of amorphous cabergoline with 0.2% (w|w) of total impurities.

Example 2

Preparation of Cabergoline Form L 6.1 g of cabergoline obtained in Example 1 were dissolved in 12 ml of 2-chlorotoluene by agitating at room temperature. The solution was cooled down to −30° C. while stirring. The gel-like material was formed after 60 minutes. Furthermore 150 ml of n-heptane were added and let stirring 1 hour at −20° C. Further the solvent was exchanged with 100 ml of fresh n-heptane, precooled to −20° C. and let stirring 1 hour at −20° C. Afterwards the temperature was raised to 10° C. (0.5 K/min) and further stirred for 1 hour, The temperature was raised to 20° C. (0.5 K/min) followed by stirring for 5 hour. The obtained dense suspension was filtered and washed with 50 ml of n-heptane and dried at 40° C. and 5 mbar for 24 hours. The obtained needle-like product (5.5 g) was identified as cabergoline form L. Particle size distribution of the product of Example 2 is the following: d 0.1=0.4 um; d 0.5=4.2 um; d 0.9=33 um.

Example 3

Preparation of Single Crystals of Cabergoline Form L

Needle-like single crystals of cabergoline form L were grown in the mother liquor (with cabergoline saturated solvent (exchanged) in Example 2), which stand at ambient temperature for 24 hours. The structure of new cabergoline form L was solved with single-crystal X-ray diffraction.

Example 4

Preparation of Cabergoline Form L from Cabergoline Form I 3.0 g of cabergoline form 1 was dissolved in 6 ml of 2-chlorotoluene by agitating at room temperature. The solution was cooled down to −30° C. while stirring. The gel-like material was formed after 60 minutes. Furthermore 70 ml of n-heptane were added and let stirring 1 hour at −20° C. Further the solvent was exchanged with 50 ml of fresh cold n-heptane and let stirring 1 hour at −20° C. Afterwards the temperature was raised to 10° C. (0.5 K/min) and further stirred for 1 hour. The temperature was raised to 20° C. followed by stirring for 5 hour. The obtained dense suspension was filtered and washed with 20 ml of n-heptane and dried at 40° C. and 5 mbar for 24 hours. To obtain about 2.6 g cabergoline form L.

Example 5

Preparation of Cabergoline Form L from Cabergoline 2-Chlorotoluene Solvate 8 g of cabergoline 2-chlorotoluene solvate was dissolved in 12 ml of 2-chlorotoluene by agitating at room temperature. The solution was cooled down to −27° C. while stirring. The gel-like material was formed after 35 minutes then 160 ml of n-heptane were added and let stirring 1 hour at −20° C. Further the solvent was exchanged with 100 ml of fresh n-heptane, precooled to −20° C. and let stirring 1 hour at −20° C. Afterwards the temperature was raised to 10° C. (0.5 K/min) and further stirred for 1 hour. The temperature was raised to 10° C. (0.5 K/min) followed by stirring for 5 hour. The obtained dense suspension was filtered and washed with 50 ml of n-heptane and dried at 40° C. and 5 mbar for 24 hours. The obtained needle-like product 5.3 g has identical physico-chemical properties as in Example 2.

Example 6

Preparation of Tablets with Active Ingredient of Cabergoline Form L

Composition Components:

| Cabergoline form L | 0.5 mg |
| Lactose | 75.9 mg |
| Leucine | 3.6 mg |

The ingredients were mixed, sieved (0.7 mm) and compressed into a tablet of the prescribed tablet weight of 80 mg.

Example A

Preparation of Cabergoline 2-Chlorotoluene Solvate 6.1 g of cabergoline obtained in example 1 were dissolved in 12 ml of 2-chlorotoluene by agitating at room temperature. The solution was cooled down to −30° C. while stirring. After 60 minutes of stirring crystalline slurry was obtained and 150 ml of n-heptane was added and let stirring 1 hour at −20° C. Further the solvent was exchanged with 100 ml of fresh n-heptane, precooled to −20° C. and let stirring 1 hour at −20° C. The obtained precipitate was filtered and 2-chlorotoluene solvate of cabergoline was obtained which was identified by XRD data.

Example B

Capturing of Cabergoline Form I Precipitate 6.1 g of cabergoline obtained in example 1 were dissolved in 12 ml of 2-chlorotoluene by agitating at room temperature. The solution was cooled down to −30° C. while stirring. The gel-like material was formed after 60 minutes. Furthermore 150 ml of n-heptane were added and let stirring 1 hour at −20° C. Further the solvent was exchanged with 100 ml of fresh n-heptane, precooled to −20° C. and let stirring 1 hour at −20° C. Afterwards the temperature was slowly raising to 0° C. (0.5 K/min) and small samples were analyzed. DSC analysis showed gradual disappearing of 2-chlorotoluene solvate and appearing of form I and later at higher temperature appearing of form L. The captured precipitate between −5-0° C. after 30 min of gradual temperature elevating and later dried at 35° C. at 5 mBar for 48 h shows mainly form I with less than 5% of form L according to DSC analysis.

The Products were Analyzed by Following Methods:
Particle size distribution was measured by the Malvern method.

X-Ray Powder Diffraction Method:
Conditions for obtaining powder X-ray diffraction (XRD) patterns: The powder x-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40 °2θ in steps of 0.033 °2θ and the measurement time of 50 seconds per step. Variable divergence and antiscatter slits were used to maintain 12 mm of sample length irradiated.

IR Spectroscopy Method:
Conditions for obtaining infrared spectra: Fourier transform infrared (FTIR) spectra were recorded with a Nicolet Nexus spectrometer. Spectra over a range of 4000 to 400 cm$^{-1}$ with a resolution of 2 cm$^{-1}$ (16 scans) were recorded on KBr tablets.

Differential Scanning Calorimetry:
Conditions for obtaining DSC thermograms: Thermograms were obtained with Mettler Toledo DSC822$^e$ differential scanning calorimeter. The sample (4-6 mg) was placed in an unsealed aluminium pan with a hole and heated at 5° C./min in the temperature range from 30° C. to 200° C.

The invention claimed is:

1. Cabergoline crystal form L, exhibiting an X-ray diffraction pattern with d-values-4.1, 5.9, 6.1, 7.4, 8.4, 12.3.

2. The cabergoline of claim 1, wherein the X ray diffraction pattern is as shown in FIG. 2.

3. The cabergoline of claim 1, having an IR spectrum absorption peak at 3377 cm$^{-1}$.

4. The cabergoline of claim 1, having an endothermic peak with onset between 105° C. and 107° C.

5. The cabergoline of claim 1, which is in the form of needles.

6. A process for the preparation of cabergoline crystal form L, exhibiting an X-ray diffraction pattern with d-values-4.1, 5.9, 6.1, 7.4, 8.4, 12.3, the process comprising the following steps:
(a) dissolving cabergoline in a halogenated aromatic solvent and optionally in a co-solvent;
(b) cooling the solution to below 0° C. to obtain suspension;
(c) adding an anti-solvent;
(d) re-warming the solution to above 0° C.; and
(e) isolating the precipitated product.

7. A process for the preparation of cabergoline crystal form L, exhibiting an X-ray diffraction pattern with d-values-4.1, 5.9, 6.1, 7.4, 8.4, 12.3, the process comprising the following steps:
(a) preparing a semi-solid cabergoline by extracting crude cabergoline, from a water/acetonitrile solution thereof into a dichloromethane organic phase, and evaporating organic solvents to obtain semi-solid cabergoline;
(b) dissolving semi-solid cabergoline in a halogenated aromatic solvent and optionally a co-solvent;

(c) cooling the solution to below 0° C. to obtain a suspension,
(d) adding an anti-solvent,
(e) rewarming the solution to above 0° C.,
(f) isolating the precipitated product.

8. The process for the preparation of cabergoline crystal form L according to claim 6 wherein cabergoline from step (a) is cabergoline solvate, amorphous cabergoline or cabergoline form I.

9. The process for the preparation of cabergoline crystal form L according to claim 6 or 7 wherein the halogenated aromatic compound is 2-chlorotoluene.

10. The process for the preparation of cabergoline crystal form L according to claim 6 or 7 wherein the co-solvent is acetonitrile in the volume of 0-10% (w/w) of total solvent mass.

11. The process for the preparation of cabergoline crystal form L according to claim 6 or 7 wherein cooling the solution to below 0° C. means cooling to below −25° C.

12. The process for the preparation of cabergoline crystal form L according to claim 6 or 7 wherein the anti-solvent is n-heptane.

13. The process for the preparation of cabergoline crystal form L according to claim 6 or 7 wherein the solution is re-warmed to 10-20° C.

14. A pharmaceutical composition comprising cabergoline crystal form L of claim 1 and pharmaceutically acceptable carrier.

* * * * *